(12) United States Patent
Tighe et al.

(10) Patent No.: US 7,968,650 B2
(45) Date of Patent: Jun. 28, 2011

(54) POLYMERIC COMPOSITIONS COMPRISING AT LEAST ONE VOLUME EXCLUDING POLYMER

(75) Inventors: Brian J. Tighe, Solihull (GB); Muriel Nasso, Putney Hill (GB); Beverley Benning, Streethy Sutton Coldfield (GB); Frank F. Molock, Jr., Orange Park, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 746 days.

(21) Appl. No.: 11/925,207

(22) Filed: Oct. 26, 2007

(65) Prior Publication Data

US 2008/0114123 A1 May 15, 2008

Related U.S. Application Data

(60) Provisional application No. 60/863,755, filed on Oct. 31, 2006.

(51) Int. Cl.
*C08F 126/06* (2006.01)

(52) U.S. Cl. ............ 525/326.7; 525/326.8; 525/326.9; 525/327.1; 525/327.2; 525/327.3; 525/327.4; 525/327.5; 525/327.6; 525/327.7; 525/327.8; 525/328.2; 525/329.5; 526/256; 526/257; 526/258; 526/259; 526/260; 526/261; 526/262; 526/263; 526/264; 526/265; 526/266; 526/267; 526/268; 526/269; 526/270; 526/271; 526/272; 526/273; 526/287; 526/288

(58) Field of Classification Search ........... 525/326.7, 525/326.8, 326.9, 327.1, 327.2, 327.3, 327.4, 525/327.5, 327.6, 327.7, 327.8, 328.2, 329.5; 526/256, 257, 258, 259, 260, 261, 262, 263, 526/264, 265, 266, 267, 268, 269, 270, 271, 526/272, 273, 287, 288
See application file for complete search history.

(56) References Cited

U.S. PATENT DOCUMENTS

| | | | |
|---|---|---|---|
| 3,497,476 A * | 2/1970 | Ulrich et al. ............... 526/263 |
| 3,717,687 A * | 2/1973 | Shanley et al. ............... 8/186 |
| 3,808,178 A | 4/1974 | Gaylord |
| 3,867,351 A | 2/1975 | Juna et al. |
| 4,120,570 A | 10/1978 | Gaylord |
| 4,136,250 A | 1/1979 | Mueller |
| 4,153,641 A | 5/1979 | Deichert |
| 4,301,012 A | 11/1981 | Puckett |
| 4,330,383 A | 5/1982 | Ellis et al. |
| 4,438,245 A * | 3/1984 | Satomura .................. 526/286 |
| 4,490,308 A * | 12/1984 | Fong et al. ............... 562/106 |
| 4,582,802 A | 4/1986 | Zimmerman et al. |
| 4,725,277 A | 2/1988 | Bissonette |
| 4,731,079 A | 3/1988 | Stoy |
| 4,740,533 A | 4/1988 | Su |
| 4,766,064 A | 8/1988 | Williams et al. |
| 4,812,544 A * | 3/1989 | Sopko et al. ............... 526/73 |
| 4,863,464 A | 9/1989 | Dusek |
| 4,872,876 A | 10/1989 | Smith |
| 4,910,277 A | 3/1990 | Bambury |
| 5,011,275 A | 4/1991 | Mueller |
| 5,034,461 A | 7/1991 | Lai |
| 5,070,215 A | 12/1991 | Bambury |
| 5,075,399 A | 12/1991 | Ahmed et al. |
| 5,212,270 A * | 5/1993 | Lal .......................... 526/287 |
| 5,321,108 A | 6/1994 | Kunzler |
| 5,387,662 A | 2/1995 | Kunzler |
| 5,451,617 A | 9/1995 | Lai |
| 5,453,461 A * | 9/1995 | Heiliger et al. ............ 525/54.1 |
| 5,539,016 A | 7/1996 | Kunzler |
| 5,679,835 A | 10/1997 | Inden et al. |
| 5,710,302 A | 1/1998 | Kunzler |
| 5,760,100 A | 6/1998 | Nicolson |
| 5,776,999 A | 7/1998 | Nicolson |
| 5,789,461 A | 8/1998 | Nicolson |
| 5,849,811 A | 12/1998 | Nicolson |
| 5,965,631 A | 10/1999 | Nicolson |
| 5,994,430 A * | 11/1999 | Ding et al. ................. 524/80 |
| 5,998,498 A | 12/1999 | Vanderlaan |
| 6,087,415 A | 7/2000 | Vanderlaan |
| 6,218,492 B1 | 4/2001 | Hill et al. |
| 6,365,692 B1 | 4/2002 | Hill et al. |
| 6,417,000 B1 | 7/2002 | Hill et al. |
| 6,451,871 B1 | 9/2002 | Winterton et al. |
| 6,689,480 B2 | 2/2004 | Shimoyama et al. |
| 6,702,983 B2 | 3/2004 | Hu |
| 6,822,016 B2 | 11/2004 | McCabe |
| 6,827,966 B2 | 12/2004 | Qiu |
| 6,849,671 B2 | 2/2005 | Steffen |
| 6,858,248 B2 | 2/2005 | Qiu |

(Continued)

FOREIGN PATENT DOCUMENTS

EP   80539   6/1983

(Continued)

OTHER PUBLICATIONS

U.S. Appl. No. 60/863,755, Johnson & Johnson Vision Care, Inc.
Volume III, Photoinitiators for Free Radical Cationic & Anionic Photopolymerization, 2nd Edition by J.V. Crivello & K. Dietliker; edited by G. Bradley; John Wiley and Sons; New York; 1998.
Synthetic Hydrogels 1, Copolymers of Hydroxyalkyl Acrylates and Methacrylates: Water Binding Studies, P H Corkhill, A M Jolly, C O Ng & B J Tighe, Polymer 1987,28,1758-1766.

*Primary Examiner* — Bernard Lipman
(74) *Attorney, Agent, or Firm* — Karen Harding

(57) ABSTRACT

The present invention relates to compositions comprising a polymeric substrate comprising at least one volume excluding polymer. In one embodiment, the present invention provides polymeric articles that are capable of acting as osmotic drivers. The articles are capable of maintaining a desired water balance by moving water in or out of a substrate to maintain cation concentration equilibrium between the substrate and its environment.

22 Claims, 3 Drawing Sheets

U.S. PATENT DOCUMENTS

| | | |
|---|---|---|
| 6,867,245 B2 | 3/2005 | Iwata et al. |
| 7,022,379 B2 | 4/2006 | Winterton et al. |
| 7,052,131 B2 | 5/2006 | McCabe et al. |
| 7,468,344 B2 | 12/2008 | Ketelson |
| 7,807,852 B2 | 10/2010 | Ricks-Laskoski |
| 2002/0016383 A1 | 2/2002 | Iwata |
| 2003/0052424 A1 | 3/2003 | Turner |
| 2003/0162862 A1 | 8/2003 | McCabe |
| 2005/0070661 A1 | 3/2005 | Molock |
| 2006/0072069 A1 | 4/2006 | Laredo |
| 2007/0197751 A1 * | 8/2007 | Baugh et al. .................. 526/266 |
| 2008/0045612 A1 | 2/2008 | Rathore et al. |

FOREIGN PATENT DOCUMENTS

| | | |
|---|---|---|
| EP | 406161 | 1/1991 |
| EP | 458245 | 11/1991 |
| EP | 0927910 | 7/1999 |
| EP | 1287060 | 3/2003 |
| JP | 6123860 | 5/1994 |
| JP | 200010055 | 1/2000 |
| WO | WO 9421698 | 9/1994 |
| WO | WO 9631792 | 10/1996 |
| WO | WO 9927978 | 6/1999 |
| WO | WO 9929750 | 6/1999 |
| WO | WO 0022459 | 4/2000 |
| WO | WO 0022460 | 4/2000 |
| WO | WO 0026698 | 5/2000 |
| WO | WO 03022321 | 3/2003 |
| WO | WO 2004060431 | 7/2004 |
| WO | WO 2004/099876 | 11/2004 |
| WO | WO 2006039276 | 4/2006 |

* cited by examiner

POLYMERIC COMPOSITIONS COMPRISING AT LEAST ONE VOLUME EXCLUDING POLYMER

RELATED APPLICATIONS

This application claims priority from U.S. provisional application Ser. No. 60/863,755, which is incorporated by reference in its entirety.

BACKGROUND OF THE INVENTION

It is known that contact lenses can be used to improve vision, and various contact lenses have been commercially produced for many years. Hydrogel contact lenses are very popular today. These lenses are often more comfortable to wear than contact lenses made of hard materials.

One popular contact lens material used for daily and weekly wear is Etafilcon, based on 2-hydroxyethyl methacrylate (HEMA) and a small amount of methacrylic acid. The acidic moiety increases the hydrophilicity of the HEMA material, making a more comfortable lens.

Contact lenses made from silicone hydrogels have been disclosed. Silicone hydrogel contact lenses allow greater amounts of oxygen than conventional lenses (such as HEMA based lenses) through the lens to the eye. However, the silicone materials are not inherently wettable, and coatings and wetting agents have been used to improve the wettability of the lens. Mucin balls are known to develop in the wearer of some silicone hydrogel contact lenses, caused by the shearing force between the eyelid and the material. The long-term effects of this have yet to be discovered.

SUMMARY OF THE INVENTION

The present invention relates to a composition comprising a polymer comprising at least one volume excluding polymer.

The present invention further relates to a device formed from a hydrated polymer and at least one volume excluding polymer in a concentration sufficient to act as an osmotic driver.

The present invention further relates to a method comprising incorporating at least one volume excluding polymer in or on at least one substrate.

DESCRIPTION OF THE INVENTION

Figure 1:
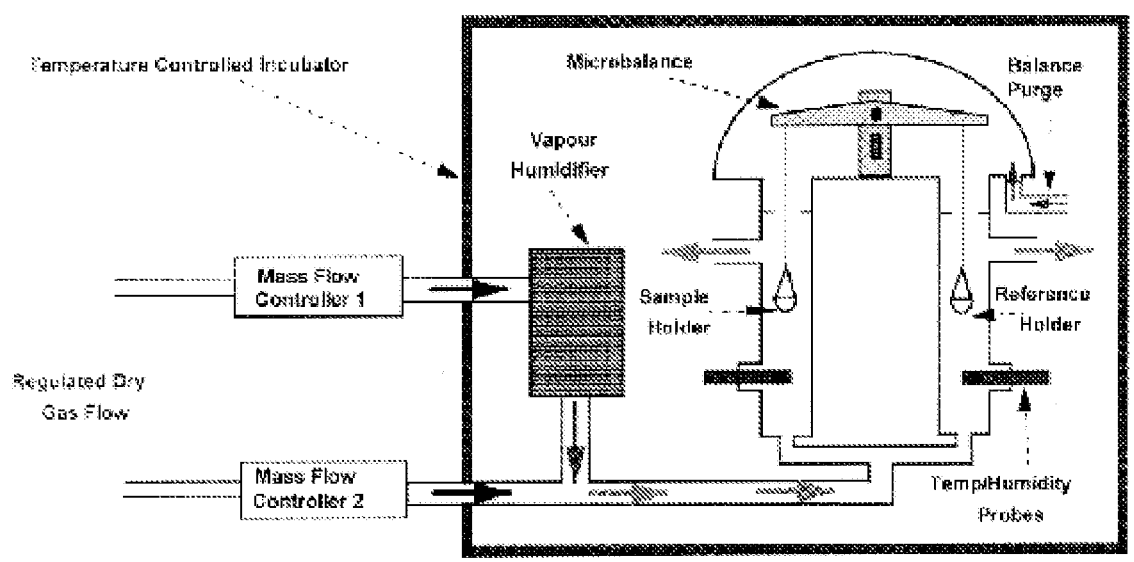
FIG. 1 is a diagram of the dynamic vapor sorption analyzer used in the Examples.

As used herein, volume excluding polymer are polymers comprising hydratable polyanions which by virtue of charge repulsion in the charged state and the size of the anionic groups have the ability to exclude other groups from the surface on which they are incorporated. In one embodiment, the hydratable polyanions will possess an excluding volume greater than that possessed by carboxylate groups at physiological pH, such as those between about 5 to about 8. Suitable anionic groups include phosphates, phosphonates, borates, sulfates, sulfonates, combinations thereof and the like. In one embodiment the anionic group comprises at least one sulfonate group. In another embodiment, the anionic group is sulfonate.

The volume excluding polymers may be formed from reactive anionic monomers which comprise the hydratable polyanion groups and at least one reactive group, which permits incorporation of the reactive anionic monomer into the volume excluding polymer.

Examples of suitable reactive anionic monomers include

R-L-A

Wherein R is a reactive group, L is a linking group and A is an anionic group as defined above.

Reactive groups, R, include groups that that can undergo free radical and/or cationic polymerization, condensation polymerization, ring opening polymerization and the like. Non-limiting examples of free radical reactive groups include (meth)acrylates, styryls, vinyls, vinyl ethers, $C_{1-6}$alkyl(meth)acrylates, (meth)acrylamides, $C_{1-6}$alkyl(meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates. Non-limiting examples of cationic reactive groups include vinyl ethers or epoxide groups and mixtures thereof. In one embodiment the reactive group comprises (meth)acrylate, acryloxy, (meth)acrylamide, and mixtures thereof. As used herein "(meth)acrylate" includes both acrylate and methacrylate.

Non-limiting examples groups capable of undergoing condensation polymerization include alcohols, esters, carboxylic acids, isocyanates, anhydrides, groups capable of halide displacement, such as phenyl chloride, combinations thereof and the like.

Non limiting examples of groups capable of undergoing ring opening polymerization include cyclic derivatives of hydroxyl and amino carboxycylic acids, cyclic ethers, cyclic esters, cyclic amides, combinations thereof and the like.

Non limiting examples of groups capable of undergoing ring opening polymerization include cyclic ethers, cyclic esters, cyclic amides, combinations thereof and the like.

L is a divalent linking group comprising substituted and unsubstituted alkylene having 1-12 carbon atoms, which may be straight or branched, polyethers, oxazolines, substituted and unsubstituted heterocyclic groups. Suitable substituents include aryl, amine, ether, amide, hydroxyl groups, combinations thereof and the like. In another embodiment, L comprises straight or branched alkylene group having 2 to 8 carbons. In one embodiment the reactive anions of the present invention have the formula

$H_2C=C(R_2)-CO_2-(CH_2)_n-A$

Wherein $R_2$ is selected from —H, —$CH_3$, —$CH_2CO_2$—$(CH_2)_n$-A, where n is an integer between 2 and 8 and A is as defined above. In one embodiment n is 2 to 6.

The reactive anionic monomers are polymerized, either alone or with comonomers to form the volume excluding polymer. Suitable volume excluding polymers may have a wide range of molecular weights, so long as the desired concentration of hydratable polyanions is present at the substrate surface. This may be accomplished by grafting oligomers of 3 or more repeat units onto the substrate or by incorporating polymer having a molecular weight within a wide range. Accordingly, the volume excluding polymer may be an oligomer having a molecular weight of at least about 500, or may be a polymer having a molecular weight of at least about 1000, and in some embodiments, between about 1000 and several million, as measured via any of the well known methods in the art such as GPC, viscosity and the like. Mixtures of volume excluding polymers having different molecular weights may also be used. For example, in some embodiments it may be desirable to use a mixture of volume excluding polymers, with each of the polymers having different molecular weights. In one non-limiting embodiment, where it is desired to have anionic groups close to the substrate surface and also spaced from the substrate surface at least two distinct volume excluding polymers, one having a relatively low molecular weight of less than about 10,000 and a second volume excluding polymer with a high molecular weight of greater than 100,000 might be used. Other combinations will be apparent to those of skill in the art using the teachings of the present invention.

The volume excluding polymers suitable for use in the present invention are hydrolytically stable, and in some embodiments thermally stable as well.

Generally a physiologically compatible cation is ionically associated to the anionic groups. When the substrate of the present invention is an ophthalmic devices such as a contact lens, suitable cations include Li+, $Na^+$, $K^+$, $NH_4^+$, $Mg^+$, $Zn^+$, Ag+, combinations thereof and the like. In some embodiments, the cations comprise $Na^+$, $K^+$, $NH_4^+$ and mixtures thereof. Additional cations may also be present as salts in the solutions which are used with the ophthalmic devices of the present invention, including but not limited to $Ca^+$, $Mg^+$, $Zn^+$, $Ag^+$ and the like.

Examples of suitable reactive anionic monomers include, but are not limited to of sodium-2-(acrylamido)-2-methylpropane sulphonate, 3-sulphopropyl (meth)acrylate potassium salt, 3-sulphopropyl (meth)acrylate sodium salt, bis 3-sulphopropyl itaconate di sodium, bis 3-sulphopropyl itaconate di potassium, vinyl sulphonate sodium salt, vinyl sulphonate salt, styrene sulfonate and mixtures thereof.

In some embodiments the volume excluding polymer may also formed from reactive anionic monomers where L comprises amine functionality. These amine functional reactive anionic monomers have a balanced charge, and may be desirable for substrates where low swelling is desired. However, to achieve the desired osmotic effect, at least about 20 wt % of the volume excluding polymer should comprise repeating units derived from the reactive anionic monomers.

The volume excluding polymers comprise between about 20 and about 80 wt % repeating units derived from reactive anionic monomer(s) and in some embodiments between about 40 and about 75 wt %.

The volume excluding polymers may also include comonomers. The comonomers may be distributed throughout the volume excluding polymer in any way, including randomly distributed, distributed in blocks or a combination thereof. In one embodiment, when comonomers are present, they are distributed through the polymer so that they do not provide substantial gaps in the volume excluded by the anionic groups. In embodiments where the volume excluding polymer is associated with the lens via affinity interactions, the volume excluding polymer may include blocks of comonomers with properties similar to those of the lens polymer. For example, for a contact lens comprising silicone, the comonomer may be a hydrophobic block, such as a hexylene, or may be a pendant hydrophobic group, such as a pendant siloxane group.

In one embodiment, the comonomers may be selected from monofunctional hydrophilic monomers, such as, but not limited to acrylic- or vinyl-containing monomers. The term "vinyl-type" or "vinyl-containing" monomers refer to monomers containing the vinyl grouping ($-CH=CH_2$) and are generally highly reactive. Such hydrophilic vinyl-containing monomers are known to polymerize relatively easily.

"Acrylic-type" or "acrylic-containing" monomers are those monomers containing the acrylic group: ($CH_2=CRCOX$) wherein R is H or $CH_3$, and X is O or N, which are also known to polymerize readily, such as N,N-dimethyl acrylamide (DMA), 2-hydroxyethyl methacrylate (HEMA), glycerol methacrylate, 2-hydroxyethyl methacrylamide, hydroxyethyl acrylamide, polyethyleneglycol mono (meth)acrylate, methacrylic acid and acrylic acid.

Hydrophilic vinyl-containing monomers which may used as the comonomers include N-vinyl amides, N-vinyl lactams (e.g. N-vinylpyrrolidone or NVP), N-vinyl acetamide, N-vinyl-N-methyl acetamide, N-vinyl-N-ethyl acetamide, N-vinyl-N-ethyl formamide, N-vinyl formamide, 2,2-di methoxy, 1-hydroxy acrylamide, hydroxymethyl diacetone acrylamide, N-acryloyl morpholine, hydroxyl methylacrylamide, combinations thereof and the like.

Other hydrophilic monomers that can be employed in the invention include polyoxyethylene polyols having one or more of the terminal hydroxyl groups replaced with a functional group containing a polymerizable double bond. Examples include polyethylene glycol, ethoxylated alkyl glucoside, and ethoxylated bisphenol A reacted with one or more molar equivalents of an end-capping group such as isocyanatoethyl methacrylate ("IEM"), toluoylmeta isocyanate (TMI), methacrylic anhydride, methacryloyl chloride, vinylbenzoyl chloride, or the like, to produce a polyethylene polyol having one or more terminal polymerizable olefinic groups bonded to the polyethylene polyol through linking moieties such as carbamate or ester groups.

Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art.

In one embodiment the comonomer comprises at least one hydrophilic monomer selected from DMA, HEMA, glycerol methacrylate, 2-hydroxyethyl methacrylamide, NVP, N-vinyl-N-methyl acrylamide, N-methyl-N-vinylacetamide, polyethyleneglycol monomethacrylate, methacrylic acid, acrylic acid, N-(tris(hydroxymethyl)methyl)acrylamide, itaconic acid and combinations thereof.

In another embodiment, the volume excluding polymer comprises comonomers containing at least one amide group, carboxyl, hydroxyl group, or mixtures thereof. Comonomers of these types may have the R-L groups defined above, and further comprise at least one amide, carboxylic acid or hydroxyl in place of the polyanionic group or may have the amide, carboxylic acid or hydroxyl group bonded directly to R, as defined above. Suitable amide groups have the structure

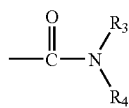

where $R_3$ and $R_4$ are independently selected from H, straight or branched $C_{1-12}$ alkyls which may be ether substituted.

In one embodiment the volume excluding polymer is formed from the following monomers in the following amounts:

| monomer | Mol. %, based upon all reactive components | | |
|---|---|---|---|
| | Embodiment 1 | Embodiment 2 | Embodiment 3 |
| Reactive anionic monomer | 2-100 | 30-60 | 40-55 |
| Amide containing comonomer | 2-80 | 15-45 | 25-45 |
| Carboxylic acid containing comonomer | 0-40 | 10-30 | 15-25 |
| Hydroxyl containing comonomer | 0-40 | 10-30 | 15-25 |

The volume excluding polymer may also comprise at least one hydrophobic comonomer in addition or instead of the above listed hydrophilic monomers. Any of the silicone monomers described below may be used as well as any other hydrophobic monomers which are known to be useful for the manufacture of biomedical devices, such as rigid or hard contact lenses or IOLs.

In some embodiments it is desirable for the volume excluding polymer to have a structure with the hydratable polyanion groups extending out from the polymer backbone. In another embodiment the hydratable polyanion groups extend out from the polymer backbone and are freely rotatable. Examples of suitable structures include a brush structure, a branched structure a loop structure and combinations thereof. In a brush structure the hydratable polyanion groups extend pendantly along the polymer backbone for form a comb or brush structure. In a branched structure, the hydratable polyanions extend pendantly from the non-reaction terminal end of the volume excluding polymer. In a loop structure the hydratable polyanion groups are bound to the backbone of the volume excluding polymer in at least two places forming a loop or bridge with the polymer backbone.

The volume excluding polymer may be used on with biomedical devices. As used herein biomedical devices include those designed to be used while in or on either or both mammalian tissue or fluid and in one embodiment human tissue or fluid. Examples of such devices include, without limitation, stents, implants, catheters, wound dressings, intervertebral disk replacements, sensor devices, diagnostic equipment and ophthalmic devices, including punctal plugs, ophthalmic lenses and ophthalmic inserts. In one embodiment, the biomedical device is an ophthalmic lens including, without limitation, contact or intraocular lenses. In another embodiment the device is a soft contact lens, and in some cases a silicone hydrogel contact lens.

The medical devices may be made from any material known to be useful therefor. In one embodiment the medical device is made from at lest one polymer. For simplicity the methods for attachment will be described with reference to one embodiment where the medical device is a contact lens. Those of skill in the art, using the teaching of the present invention will be able to apply the present invention to other medical devices.

The volume excluding polymer may be covalently or ionically attached to at least a portion of at least one surface of the substrate, may be incorporated into a coating composition which applied to the surface of the substrate, may be imbibed into all or part of the substrate or may be polymerized with the reactive mixture from which the substrate is made, or a combination of the above methods.

In embodiments where the volume excluding polymer is covalently attached, both the substrate polymer and the volume excluding polymer will have reactive groups capable of reacting to form a covalent bond. Any method capable of forming a covalent bond which will remain stable during the use of the substrate may be used. According, free radical reactions, condensation and esterification reactions, ring opening reactions, and the like. If the substrate polymer does not have the appropriate reactive groups it can be pretreated to generate the desired groups. In one embodiment, the volume excluding polymer comprising a free radical reactive compound, and is contacted with at least one surface of the substrate in coating effective amounts and under coating effective conditions to coat the desired substrate surface.

The volume excluding polymer may be incorporated in to a solution to facilitate the coating process. For example, the volume excluding polymer and any other desired components such as initiators, crosslinkers, colorants, photochromic compounds, stabilizers, chain transfer agents, humectants, wetting agents, antimicrobial compounds, therapeutic compounds, combinations thereof and the like may be combined in a solvent. In some embodiments, it may be desirable for certain of the additional compounds, such as, but not limited to humectants, wetting agents, antimicrobial compounds, therapeutic compounds and mixtures thereof to elute from the article. Suitable solvents will dissolve the volume excluding polymer and other coating composition components, but will not dissolve or substantially swell the biomedical device. For example, when the biomedical device is a contact lens, suitable examples of solvents include water, acetonitrile, water miscible alcohols, polyethers, combinations thereof and the like. Specific examples include alkoxy alcohols, alkoxy polyols, glycerol borate esters, combinations thereof and the like. Specific examples include tripropylene glycol, ethoxy ethanol, methoxy ethanol, dipropylene glycol, propylene glycol, alkoxy trimethylene glycol, N-propanol, isopropanol, t-amyl alcohol, t-butanol, monoethyl ether, combinations thereof and the like.

The volume excluding polymer is incorporated in the solvent in a coating effective amount. As used herein a coating effective amount is an amount sufficient to provide a coherent coating on the article surface. The coating effective amount will vary depending on the type of coating process selected. For example, for solution grafting amounts from about 5 weight %, and in some embodiments between about 5 and about 10 weight % based upon all components in the coating solution. Those of skill in the art will be able to determine suitable ranges for other coating processing using the teachings of this invention.

The biomedical device is contact with the solution via any convenient means. Suitable contacting means include spraying, dipping, wiping, rolling, combinations thereof and the like. The entire device may be coated, one surface of a device may be coated or only a portion of a surface may be coated. For example, when the biomedical device is a contact lens, the entire lens may be coated, only one side of the lens may be coated (for example either the back curve which rests on the cornea and conjuctiva, or the front surface which is in contact with the eyelids and air), or only a portion of a surface may be coated (for example a portion of either surface which covers the iris, pupil or conjuctiva).

The device is contacted with the solvent/coating polymer solution under conditions suitable to form the coating. Suitable temperatures include those between the freezing and boiling points of the selected solvent, preferably between about 0 and about 100° C. and more preferably between about 15 and about 50° C. The contact time used will be a length of time sufficient to coat the surface to the extent desired. Contact times may be up to about 2 days, in some embodiments up to about 1 day, and in some embodiments up to about 12 hours, and in another embodiment up to about 1 hour. Pressure is not critical in the coating reaction of the present invention. However, those of skill in the art will recognize that elevated pressures and temperatures may enable the reaction to be conducted in a shorter period of time. It should be appreciated that the concentration of the hydratable polyanion in the graft solution, reaction temperature and time are all related, and that higher concentrations of hydratable polyanion and/or increased temperatures may allow for shorter reaction times.

Alternatively, the reactive polyanion groups may be contacted with the substrate under polymerization effective conditions, and polymerized in the presence of the substrate. Suitable polymerization conditions will depend on the reactive polyanion groups selected. For example, for substrates containing hydroxyl groups at or near the surface free radical reactive hydratable polyanions, such as the potassium salt of 3-sulfopropylester acrylate (SPA), may be graft polymerized using a catalyst which can abstract hydrogen atoms from adjacent hydroxyl groups such as ammonium cerium (IV) nitrate (CAN). However, any known grafting techniques which creates reactive sites on the desired substrate may be used. The SPA and catalyst are mixed is a solvent which swells the selected substrate to form a graft solution. The concentration of reactive polyanion groups may vary from about 5 to about 100 weight %, and in some embodiments from about 50 to about 100 weight % in the coating solution. The catalyst is present in amounts between about 0.01 and about 1 weight % and in some embodiments between about 0.05 and about 0.1 weight % based upon the weight of the catalyst and volume excluding polymer components (reactive anionic monomers and comonomers).

Crosslinkers may be included in the coating solutions of the present application. The amount of crosslinker included will vary depending upon the article substrate selected. For examples, where the substrate is formed from a polymer having an anionic charge, the selected catalyst may penetrate the substrate polymer network and no crosslinker, or very little crosslinker may need to be used. In other embodiments, where the substrate is formed from a polymer having a neutral charge, it may be desirable to include at least one crosslinker in the coating solution in an amount sufficient to provide the desired level of coating integrity and permanence of coating between the volume excluding polymer and the substrate for the intended end use. For example, in an embodiment where the substrate is a contact lens, the coating should remain throughout the wear schedule, and should have the integrity necessary to provide the desired benefit across the relevant portion of the lens surface. When a crosslinker is used, Suitable crosslinker concentrations include from 0 to about 3 weight % and in some embodiments from about 0 to about 1%. Suitable crosslinkers include, but are not limited to dicapped polyethylene glycols, more specific examples include methylene bisacrylamide, ethylene glycol dimethacrylate, polyethylgycol dimethacrylate, tetraethylene GDMA, diallyl tartramide, pentaerithratol diacrylate, divinyl benzene combinations thereof and the like.

For water swellable substrates, such as soft contact lenses, the water content of the substrate may also affect efficiency of the graft reaction. Accordingly it may be desirable to adjust the level of grafting to achieve desired effect, or to coat the substrate with volume excluding polymer having a molecular weight which is sufficiently high to prevent it from substantially intercalating into the substrate polymer network.

The grafting process may optionally include a pre-reactive step to provide the substrate with properties which will enhance the efficiency of grafting. For example, the substrate may be treated to increase the concentration of reactive groups. Suitable preactivation steps are known in the art and include oxidation process which produces reactive sites, including but not limited to plasma oxidation, reaction with potassium persulfate, reaction with iodate, combinations thereof and the like.

Alternatively, R may be any group capable of being activated by a coupling agent, or any group capable of reacting with a substrate surface which has been activated by a coupling agent. For example, a direct reaction may be accomplished by the use of a reagent or reaction that activates a group in the surface polymer or volume the synthetic antimicrobial peptide making it reactive with a functional group on the peptide or polymer, respectively, without the incorporation of a coupling agent. For example, one or more amine or alcohol or thiol groups on the synthetic antimicrobial peptide may be reacted directly with isothiocyanate, acyl azide, N-hydroxysuccinimide ester, pentafluorophenoxy ester, sulfonyl chloride, an aldehyde, glyoxal epoxide, carbonate, aryl halide, imido ester, tosylate ester or an anhydride group on the polymer.

In an alternative embodiment, coupling agents may be used. Coupling agents useful for coupling the cationic peptide or protein to the device's surface include, without limitation, N,N'-carbonyldiimidazole, carbodiimides such as 1-ethyl-3-(3-dimethylaminopropyl)carbodiimide ("EDC"), dicyclohexyl carbodiimide, 1-cylcohexyl-3-(2-morpholinoethyl) carbodiimide, diisopropyl carbodiimide, or mixtures thereof. The carbodiimides also may be used with N-hydroxysuccinimide or N-hydroxysulfosuccinimide to form esters that can react with amines to form amides.

Amino groups also may be coupled to the polymer by the formation of Schiff bases that can be reduced with agents such as sodium cyanoborohydride and the like to form hydrolytically stable amine links. Coupling agents useful for this purpose include, without limitation, N-hydroxysuccinimide esters, such as dithiobis(succinimidylpropionate), 3,3'-dithiobis(sulfosuccinimidylpropionate), disuccinimidyl suberate, bis(sulfosuccinimidyl) suberate, disuccinimidyl tartarate and the like, imidoesters, including, without limitation, dimethyl adipimate, difluorobenzene derivatives, including without limitation 1,5-difluoro-2,4-dinitrobenzene, bromofunctional aldehydes, including without limitation gluteraldehyde, and bis epoxides, including without limitation 1,4-butanediol diglycidyl ether. One ordinarily skilled in the art will recognize that any number of other coupling agents may be used depending on the functional groups present on the device's surface.

If the device's surface does not contain suitable reactive groups, such suitable groups may be incorporated into the polymer by any conventional organic synthesis methods. Alternatively, the reactive groups may be introduced by the addition of polymerizable monomers containing reactive groups into the monomer mixture used to form the polymer. As are known by those in the art, any monomer with a labile hydrogen, such but not limited to hydroxyl group, acid, acid chloride groups, carbodiimides, amines and the like, may be used. Reactive gas plasma processes may also be used.

Alternatively, the volume excluding polymer may be associated with polymer substrate. The volume excluding polymer may be associated via ionic interactions, steric interactions, affinity interactions, adsorbtion, dispersive interactions, anionic charges, interpenetration, combinations thereof and the like. In this embodiment, the comonomers in the volume excluding polymer are selected to provide the desired interaction. In this process the polymer substrate is contacted with a solution comprising the volume excluding polymer under conditions which allow incorporation of the volume excluding polymer in the desired amount. Methods such as those disclosed in U.S. Pat. Nos. 6,689,480, 6,827, 966, 6,451,871, 7,022,379, 6,858,248, WO 2004,060431 and EP 1,287,060, the disclosures of which, and all other patents and applications listed herein, is incorporated herein by reference.

In another embodiment the volume excluding polymer may be incorporated via a mold transfer process. Generally the mold transfer process would be used to incorporate the volume excluding polymer as follows: coating a molding surface of a mold or a mold half with a coating effective amount of a coating composition comprising at least one volume excluding polymer; b.) dispensing the reaction mixture comprising the polymerizable components selected to make the desired substrate into the mold or mold half, and c.) curing under conditions suitable to form the desired substrated coated with the coating composition. In some embodiments it may be desired to select the coating composition such that it will swell in the substrate reaction mixture. Further details relating to mold transfer coating may be found in US-2003-0052424.

Other coating methods will be apparent to those of skill in the art, and are within the scope of the present invention.

In one embodiment, the volume excluding polymer is incorporated on at least one surface of the substrate in an amount effective to prevent or resist dehydration of that surface of the substrate. For example, in one embodiment where the substrate is a contact lens, the front surface of the contact lens, which is in contact with the eyelids during blinking, comprises a layer of at least one anionic volume excluding polymer. The polyanions in the volume excluding polymer associate with cations from the tear film. As the water on the front surface of the contact lens evaporates, the concentration of cations in the tear film on the lens surface increases above the concentration of cations in the tears. This creates an osmotic imbalance, which draws water from the tear film to restore the equilibrium concentration of cations to the water on the front lens surface. Thus, in one embodiment, the volume excluding polymers of the present invention act as osmotic drivers. As used herein, osmotic drivers are components that move water in or out of a substrate to maintain cation concentration equilibrium between the substrate and its environment.

The amount of water drawn from the tear film to the front surface of the lens may be controlled by the thickness of the coating of volume excluding polymer. In embodiments where the device is an ophthalmic device adapted to rest between the cornea or conjunctiva and any part of the eyelids, the volume excluding polymer is located primarily on the outer 5 um of the lens surface. Lenses with thicker layers or may have a tendency to pull undesirable amounts of water from the tear fluid. Thus, another embodiment of the present invention includes devices which act as osmotic drivers, maintaining a desired water balance on or in the device. Other end uses for such osmotic drivers include, but are not limited to wound healing materials, including dressings, and therapeutic ophthalmic dressings, intervertebral disk replacements and the like.

Examples of polymers which may be used to form substrates suitable for the present invention include, without limitation, polymers and copolymers of styrene and substituted styrenes, ethylene, propylene, acrylates and methacrylates, N-vinyl lactams, acrylamides and methacrylamides, acrylonitrile, acrylic and methacrylic acids as well as polyurethanes, polyesters, polydimethylsiloxanes and mixtures thereof. Such polymers may include hydrogels and silicone hydrogels.

In one embodiment where the biomedical device is a contact lens, suitable polymers include polymers used to make soft contact lenses, and those used to make hard contact lenses. Non-limiting examples of suitable soft contact lens formulations of include polymers and copolymers of poly (meth)acrylates, including but not limited to silicone (meth) acrylates; poly(meth)acrylamides, polyvinylcarbonates, polyvinylcarbamates, polyvinylamides, polyvinyllactams, polyurethanes, polyvinyl alcohols and combinations thereof, and those formulations described in U.S. Pat. No. 5,710,302, WO 9421698, EP 406161, U.S. Pat. No. 5,998,498, U.S. Pat. No. 6,087,415, U.S. Pat. No. 5,760,100, U.S. Pat. No. 5,776, 999, U.S. Pat. No. 5,789,461, U.S. Pat. No. 5,849,811, and U.S. Pat. No. 5,965,631. Non-limiting examples of soft contact lenses formulations include but are not limited to the formulations of acquafilcon A, balafilcon A, galyfilcon A, senofilcon A, comfilcon and lotrafilcon A and B. Additional examples of suitable silicone hydrogels include those disclosed in U.S. Pat. No. 5,998,498, WO03/22321, U.S. Pat. No. 6,087,415, U.S. Pat. No. 5,760,100, U.S. Pat. No. 5,776, 999, U.S. Pat. No. 5,789,461, U.S. Pat. No. 5,849,811, U.S. Pat. No. 5,965,631, U.S. Pat. No. 6,867,245, U.S. Pat. No. 6,822,016, U.S. Pat. No. 6,849,671, U.S. Pat. No. 7,052,131. These patents as well as all other patent disclosed in this paragraph are hereby incorporated by reference in their entirety. Where the medical device is a soft contact lens, the polymer will preferably be a hydrogel, and in some embodiments will have water contents of at least about 5% and in some embodiments at least about 20%.

Hard contact lenses are made from polymers that include but are not limited to polymers and copolymers of poly(methyl)methacrylate, silicone (meth)acrylates, fluoro(meth) acrylates, fluoroethers, polyacetylenes, and polyimides, where the preparation of representative examples may be found in JP 200010055, JP 6123860 and U.S. Pat. No. 4,330, 383. Intraocular lenses of the invention can be formed using known materials. For example, the lenses may be made from a rigid material including, without limitation, polymethyl methacrylate, polystyrene, polycarbonate, or the like, and combinations thereof. Additionally, flexible materials may be used including, without limitation, hydrogels, silicone materials, acrylic materials, fluorocarbon materials and the like, or combinations thereof. Typical intraocular lenses are described in WO 0026698, WO 0022460, WO 9929750, WO 9927978, WO 0022459. U.S. Pat. Nos. 4,301,012; 4,872,876; 4,863,464; 4,725,277; 4,731,079. All of the references mentioned in this application are hereby incorporated by reference in their entirety.

In one embodiment the substrate is formed from a reactive mixture comprising at least one silicone containing component.

The term component includes monomers, macromers and prepolymers. "Monomer" refers to lower molecular weight compounds that can be polymerized to higher molecular weight compounds, polymers, macromers, or prepolymers. The term "macromer" as used herein refers to a high molecular weight polymerizable compound. Prepolymers are partially polymerized monomers or monomers which are capable of further polymerization.

A "silicone-containing component" is one that contains at least one [—Si—O—] unit in a monomer, macromer or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups. Examples of silicone-containing components which are useful in this invention may be found in U.S. Pat. Nos. 3,808,178; 4,120,570; 4,136,250; 4,153,641; 4,740,533; 5,034,461 and 5,070,215, and EP080539. These references disclose many examples of olefinic silicone-containing components.

Suitable silicone containing components include compounds of Formula I

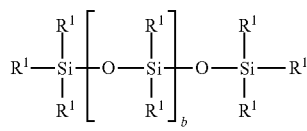

where $R^1$ is independently selected from monovalent reactive groups, monovalent alkyl groups, or monovalent aryl groups, any of the foregoing which may further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, alkoxy, amido, carbamate, halogen or combinations thereof;

where b=0 to 500, where it is understood that when bis other than 0, b is a distribution having a mode equal to a stated value;

wherein at least one $R^1$ comprises a monovalent reactive group, and in some embodiments between one and 3 $R^1$ comprise monovalent reactive groups.

As used herein "monovalent reactive groups" are groups that can undergo free radical and/or cationic polymerization. Non-limiting examples of free radical reactive groups include (meth)acrylates, styryls, vinyls, vinyl ethers, $C_{1-6}$alkyl(meth)acrylates, (meth)acrylamides, $C_{1-6}$alkyl(meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenylC$_{1-6}$alkyls, O-vinylcarbamates and O-vinylcarbonates. Non-limiting examples of cationic reactive groups include vinyl ethers or epoxide groups and mixtures thereof. In one embodiment the free radical reactive groups comprises (meth)acrylate, acryloxy, (meth)acrylamide, and mixtures thereof.

Suitable monovalent alkyl and aryl groups include unsubstituted monovalent $C_1$ to $C_{16}$alkyl groups, $C_6$-$C_{14}$ aryl groups, such as substituted and unsubstituted methyl, ethyl, propyl, butyl, 2-hydroxypropyl, propoxypropyl, polyethyleneoxypropyl, combinations thereof and the like.

In one embodiment bis zero, one $R^1$ is a monovalent reactive group, and at least 3 $R^1$ are selected from monovalent alkyl groups having one to 16 carbon atoms, and in another embodiment from monovalent alkyl groups having one to 6 carbon atoms. Non-limiting examples of silicone components of this embodiment include 2-methyl-2-hydroxy-3-[3-[1,3,3,3-tetramethyl-1-[(trimethylsilyl)oxy]disiloxanyl]propoxy]propyl ester ("SiGMA"), 2-hydroxy-3-methacryloxypropyloxypropyl-tris(trimethylsiloxy)silane, 3-methacryloxypropyltris(trimethylsiloxy)silane ("TRIS"), 3-methacryloxypropylbis(trimethylsiloxy)methylsilane and 3-methacryloxypropylpentamethyl disiloxane.

In another embodiment, bis 2 to 20, 3 to 15 or in some embodiments 3 to 10; at least one terminal $R^1$ comprises a monovalent reactive group and the remaining $R^1$ are selected from monovalent alkyl groups having 1 to 16 carbon atoms, and in another embodiment from monovalent alkyl groups having 1 to 6 carbon atoms. In yet another embodiment, bis 3 to 15, one terminal $R^1$ comprises a monovalent reactive group, the other terminal $R^1$ comprises a monovalent alkyl group having 1 to 6 carbon atoms and the remaining $R^1$ comprise monovalent alkyl group having 1 to 3 carbon atoms. Non-limiting examples of silicone components of this embodiment include (mono-(2-hydroxy-3-methacryloxypropyl)-propyl ether terminated polydimethylsiloxane (400-1000 MW)) ("OH-mPDMS"), monomethacryloxypropyl terminated mono-n-butyl terminated polydimethylsiloxanes (800-1000 MW), ("mPDMS").

In another embodiment bis 5 to 400 or from 10 to 300, both terminal $R^1$ comprise monovalent reactive groups and the remaining $R^1$ are independently selected from monovalent alkyl groups having 1 to 18 carbon atoms which may have ether linkages between carbon atoms and may further comprise halogen.

In another embodiment, one to four $R^1$ comprises a vinyl carbonate or carbamate of the formula:

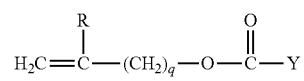

Formula II wherein: Y denotes O—, S— or NH—;

R denotes, hydrogen or methyl; d is 1, 2, 3 or 4; and q is 0 or 1.

The silicone-containing vinyl carbonate or vinyl carbamate monomers specifically include: 1,3-bis[4-(vinyloxycarbonyloxy)but-1-yl]tetramethyl-disiloxane; 3-(vinyloxycarbonylthio) propyl-[tris(trimethylsiloxy)silane]; 3-[tris(trimethylsiloxy)silyl]propyl allyl carbamate; 3-[tris(trimethylsiloxy)silyl]propyl vinyl carbamate; trimethylsilylethyl vinyl carbonate; trimethylsilylmethyl vinyl carbonate, and

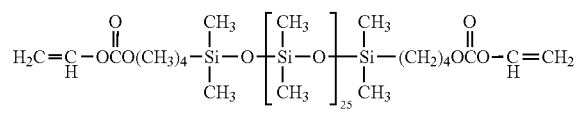

Where biomedical devices with modulus below about 200 are desired, only one $R^1$ shall comprise a monovalent reactive group and no more than two of the remaining $R^1$ groups will comprise monovalent siloxane groups.

In one embodiment, where a silicone hydrogel lens is desired, the lens of the present invention will be made from a reactive mixture comprising at least about 20 and preferably between about 20 and 70% wt silicone containing components based on total weight of reactive monomer components from which the polymer is made.

Another class of silicone-containing components includes polyurethane macromers of the following formulae:

(*D*A*D*G)$_a$*D*D*E$^1$;

E(*D*G*D*A)$_a$*D*G*D*E$^1$ or;

E(*D*A*D*G)$_a$*D*A*D*E$^1$       Formulae IV-VI wherein:
D denotes an alkyl diradical, an alkyl cycloalkyl diradical, a cycloalkyl diradical, an aryl diradical or an alkylaryl diradical having 6 to 30 carbon atoms,
G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;
* denotes a urethane or ureido linkage;
$a$ is at least 1;
A denotes a divalent polymeric radical of formula:

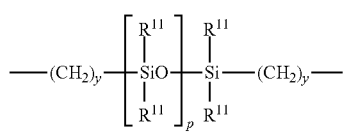

Formula VII $R^{11}$ independently denotes an alkyl or fluoro-substituted alkyl group having 1 to 10 carbon atoms which may contain ether linkages between carbon atoms; y is at least 1; and p provides a moiety weight of 400 to 10,000; each of E and $E^1$ independently denotes a polymerizable unsaturated organic radical represented by formula:

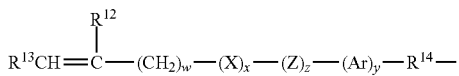

Formula VIII wherein: $R^{12}$ is hydrogen or methyl; $R^{13}$ is hydrogen, an alkyl radical having 1 to 6 carbon atoms, or a —CO—Y—$R^{15}$ radical wherein Y is —O—, Y—S— or —NH—; $R^{14}$ is a divalent radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1.

A preferred silicone-containing component is a polyurethane macromer represented by the following formula:

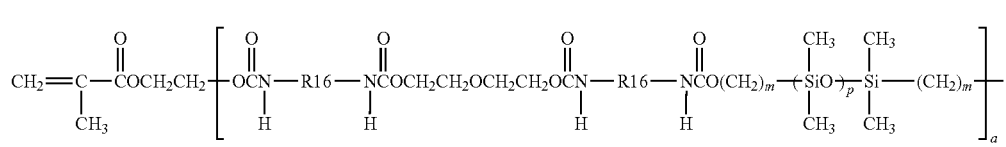

Formula IX

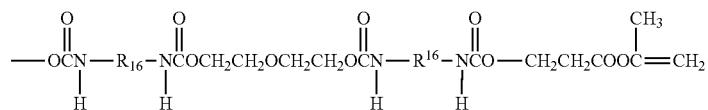

wherein $R^{16}$ is a diradical of a diisocyanate after removal of the isocyanate group, such as the diradical of isophorone diisocyanate. Another suitable silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

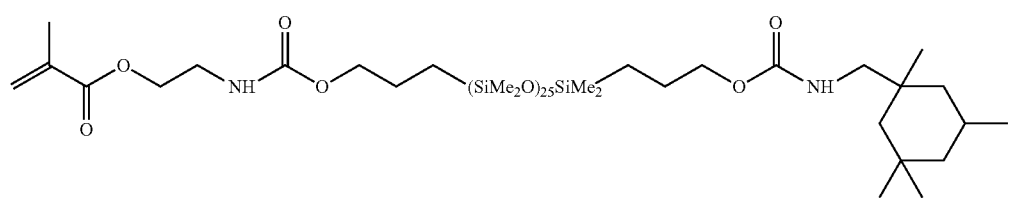

Formula X

-continued

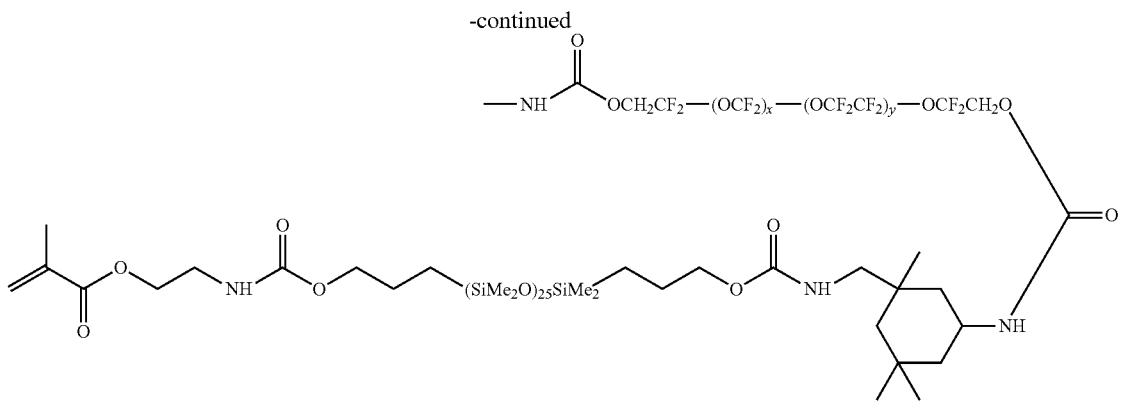

Other silicone containing components suitable for use in this invention include those described is WO 96/31792 such as macromers containing polysiloxane, polyalkylene ether, diisocyanate, polyfluorinated hydrocarbon, polyfluorinated ether and polysaccharide groups. U.S. Pat. Nos. 5,321,108; 5,387,662 and 5,539,016 describe polysiloxanes with a polar fluorinated graft or side group having a hydrogen atom attached to a terminal difluoro-substituted carbon atom. US 2002/0016383 describe hydrophilic siloxanyl methacrylates containing ether and siloxanyl linkages and crosslinkable monomers containing polyether and polysiloxanyl groups. Any of the foregoing polysiloxanes can also be used as the silicone containing component in this invention.

The reactive mixture may also comprise at least one hydrophilic component. Hydrophilic monomers can be any of the hydrophilic monomers known to be useful to make hydrogels.

One class of suitable hydrophilic monomers include acrylic- or vinyl-containing monomers. Such hydrophilic monomers may themselves be used as crosslinking agents, however, where hydrophilic monomers having more than one polymerizable functional group are used, their concentration should be limited as discussed above to provide a contact lens having the desired modulus. The term "vinyl-type" or "vinyl-containing" monomers refer to monomers containing the vinyl grouping (—CH=CH$_2$) and are generally highly reactive. Such hydrophilic vinyl-containing monomers are known to polymerize relatively easily.

"Acrylic-type" or "acrylic-containing" monomers are those monomers containing the acrylic group: (CH$_2$=CRCOX) wherein R is H or CH$_3$, and X is O or N, which are also known to polymerize readily, such as N,N-dimethyl acrylamide (DMA), 2-hydroxyethyl methacrylate (HEMA), glycerol methacrylate, 2-hydroxyethyl methacrylamide, polyethyleneglycol monomethacrylate, methacrylic acid and acrylic acid.

Hydrophilic vinyl-containing monomers which may be incorporated into the silicone hydrogels of the present invention include monomers such as N-vinyl amides, N-vinyl lactams (e.g. N-vinylpyrrolidone or NVP), N-vinyl-N-methyl acetamide, N-vinyl-N-ethyl acetamide, N-vinyl-N-ethyl formamide, N-vinyl formamide, with NVP being preferred.

Other hydrophilic monomers that can be employed in the invention include polyoxyethylene polyols having one or more of the terminal hydroxyl groups replaced with a functional group containing a polymerizable double bond. Examples include polyethylene glycol, ethoxylated alkyl glucoside, and ethoxylated bisphenol A reacted with one or more molar equivalents of an end-capping group such as isocyanatoethyl methacrylate ("IEM"), methacrylic anhydride, methacryloyl chloride, vinylbenzoyl chloride, or the like, to produce a polyethylene polyol having one or more terminal polymerizable olefinic groups bonded to the polyethylene polyol through linking moieties such as carbamate or ester groups.

Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art.

In one embodiment the hydrophilic monomer comprises at least one of DMA, HEMA, glycerol methacrylate, 2-hydroxyethyl methacrylamide, NVP, N-vinyl-N-methyl acrylamide, N-methyl-N-vinylacetamide, polyethyleneglycol monomethacrylate, methacrylic acid and acrylic acid, In one embodiment the hydrophilic monomer comprises DMA.

The hydrophilic monomers may be present in a wide range of amounts, depending upon the specific balance of properties desired. Amounts of hydrophilic monomer up to about 50 and preferably between about 5 and about 50 weight %, based upon all components in the reactive components are acceptable. For example, in one embodiment lenses of the present invention comprise a water content of at least about 30%, and in another embodiment between about 30 and about 70%. For these embodiments, the hydrophilic monomer may be included in amounts between about 20 and about 50 weight %.

Reactive and non-reactive wetting agents disclosed in US2003/0162862, US2008/0045612, US2006/0072069, WO2006/039276 may also be included. When wetting agents are used it may also be desirable to include a compatibilizing component. Suitable compatiblizing components include those meeting the compatibility test disclosed in US2003/0162862. Any of the silicone components described above may be converted into compatibilizing components by incorporating compatibilizing groups, such as hydroxyl groups, in their structure. In some embodiments, the Si to OH ratio is less than about 15:1, and in others between about 1:1 to about 10:1. Non-limiting examples of compatibilizing components include (mono-(2-hydroxy-3-methacryloxypropyl)-propyl ether terminated polydimethylsiloxane (400-1000 MW)), "OH-mPDMS", 2-methyl-, 2-hydroxy-3-[3-[1,3,3,3-tetramethyl-1-[(trimethylsilyl)oxy]disiloxanyl]propoxy]propyl ester "SiGMA", 2-hydroxy-3-methacryloxypropyloxypropyl-tris(trimethylsiloxy)silane, combinations thereof and the like.

Additional components such as, colorants, photochromic compounds, stabilizers, chain transfer agents, humectants, wetting agents, antimicrobial compounds, therapeutic compounds, combinations thereof and the like may also be included in the reactive mixture. In some embodiments, it may be desirable for certain of the additional compounds, such as, but not limited to humectants, wetting agents, antimicrobial compounds, therapeutic compounds and mixtures thereof to elute from the article.

A polymerization catalyst may be included in the reaction mixture. The polymerization initiators includes compounds such as lauryl peroxide, benzoyl peroxide, isopropyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphineoxide (Irgacure 819), 2,4,6-trimethylbenzyldiphenyl phosphine oxide and 2,4,6-trimethylbenzoyl diphenylphosphine oxide, benzoin methyl ester and a combination of camphorquinone and ethyl 4-(N,N-dimethylamino)benzoate. Commercially available visible light initiator systems include Irgacure 819, Irgacure 1700, Irgacure 1800, Irgacure 819, Irgacure 1850 (all from Ciba Specialty Chemicals) and Lucirin TPO initiator (available from BASF). Commercially available UV photoinitiators include Darocur 1173 and Darocur 2959 (Ciba Specialty Chemicals). These and other photoinitators which may be used are disclosed in Volume III, Photoinitiators for Free Radical Cationic & Anionic Photopolymerization, $2^{nd}$ Edition by J. V. Crivello & K. Dietliker; edited by G. Bradley; John Wiley and Sons; New York; 1998. The initiator is used in the reaction mixture in effective amounts to initiate photopolymerization of the reaction mixture, e.g., from about 0.1 to about 2 parts by weight per 100 parts of reactive monomer. Polymerization of the reaction mixture can be initiated using the appropriate choice of heat or visible or ultraviolet light or other means depending on the polymerization initiator used. Alternatively, initiation can be conducted without a photoinitiator using, for example, e-beam. However, when a photoinitiator is used, the preferred initiators are bisacylphosphine oxides, such as bis(2,4,6-trimethylbenzoyl)-phenyl phosphine oxide (Irgacure 819®) or a combination of 1-hydroxycyclohexyl phenyl ketone and bis(2,6-dimethoxybenzoyl)-2,4-4-trimethylpentyl phosphine oxide (DMBAPO), and in another embodiment the method of polymerization initiation is via visible light activation. A preferred initiator is bis(2,4,6-trimethylbenzoyl)-phenyl phosphine oxide (Irgacure 819®).

These reactive mixtures may be reacted "neat" or in the presence of a diluent. Suitable diluents and reaction conditions are known in the art.

In the examples the following test methods were used.

Advancing and receding contact angles were measured on a digital balance (WHITE Electrical Instruments) together with a moving stage (Ealing Optical Co) which enabled the effective force during immersion and emersion to be obtained. The contact lens samples were cut into strips of 3.3 mm wide. A maximum of 3 strips can be cut off one contact lens. Then a load is hooked at one extremity of the strip and crocodile clip clamps the other extremity (weight+hook=88.9±0.5 mg). This allowed the sample to remain straight during the analysis and prevent the lens from floating in the probe solution or curling. The advancing and receding contact angles were determined by reading the force at the point of immersion and emersion of the sample and were calculated using Young's equation:

$$\cos\theta_{a/r} = \frac{F}{\gamma P}$$

where:
F=measured force (mN)
$\theta_{a/r}$=advancing/receding contact angle (°)
γ=surface tension of probe solution (mN/m)
P=perimeter of test strip (m)

The hysteresis was calculated by subtracting the receding contact angle from the advancing contact angle.

The sessile drop contact angles reported in Examples 24-27 were measured using an automated Digidrop Contact Angle meter and technique (GBX Scientific Instruments, Romans, France)

The equilibrium water contents were measured in phosphate buffered saline at 20° C. using the technique described in Synthetic Hydrogels 1, Copolymers of Hydroxyalkyl Acrylates and Methacrylates: Water Binding Studies, P H Corkhill, A M Jolly, C O Ng & B J Tighe, Polymer 1987, 28, 1758-1766.

It will be appreciated that all of the tests specified herein have a certain amount of inherent test error. Accordingly, results reported herein are not to be taken as absolute numbers, but numerical ranges based upon the precision of the particular test.

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

In the examples, the following abbreviations are used:
AA=acrylic acid
ACMO=acryloylmorpholine
Am=acrylamide
AMO=morpholino acrylamide
CAN=ammonium cerium (IV) nitrate
DAT=diallyl tartramide
DMA=N,N-dimethylacrylamide
DMAEMA=N,N-dimethylaminoethyl methacrylate
HEA=2-hydroxyethyl acrylamide
HPA=2-hydroxy propylacrylate
NaAMPS=sodium-2-(acrylamido)-2-methylpropane sulphonate
NaVS=sodium vinylsulfonate
NIPA=N-isopropyl acrylamide
NIPAm=N-isopropylacrylamide
NVA=N-vinylacetamide
NVMA=N-methyl-N-vinylacetamide
NVP=N-vinyl pyrrolidone
PBS=phosphate buffered saline solution
SPA=3-sulphopropyl acrylate potassium salt
THFA=tetrahydrofurfuryl methacrylate
TRIS=N-(tris(hydroxymethyl)methyl)acrylamide

EXAMPLES

Examples 1-23

Grafting solutions were formed by mixing methylene bisacrylamide with water to 0.5 weight %. The reactive anionic monomer listed in Table 1, below, and CAN, were added in the amounts listed in Table 1. Three different lenses Lenefilcon A, lenses made according to Example 2 of US-2005-0070661 lenses; Dailies (Nelfilcon A, a PVA based contact lens commercially available from CibaVision) and SeeQuence (Polymacon, a polyHEMA based contact lens commercially Bausch and Lomb) were contacted with a grafting solution for the time and at the temperature listed in Table 1 and out-gassed with nitrogen. Each of the grafting solution mixtures (Examples 5, 8, 10, 15 and 20), were a 50:50 molar mixture of the listed monomers. The lenses were removed from the grafting solution and placed in distilled water for 3-5 days. The dynamic contact angle was measured and is reported in Table 1, below. The dynamic contact angle for control lenses which were not contacted with the grafting solution were also measured and are reported in Table 1, below.

1, 3, 4, 9 and 10. Graft polymerization of both SPA and NaAMPS showed dramatically lower advancing contact angles and hystersis values. The appropriate control for comparison is Comparative Example 2 (nelfilcon lens that was washed with saline for a similar period to that used in the grafting process). As shown from comparing CE1 and CE2, the washing step reduces the effect of leachable polyvinyl alcohol on the hysteresis.

On the lenefilcon lenses, modification with both SPA and NaAMPS provided lenses with improved hysteresis (Examples 12, 13 and 17-19). When NaAMPS was used as the volume excluding polymer better hysteresis was obtained where reaction conditions were more vigorous (i.e. at higher reaction temperatures of 50° C. or 60° C., longer reaction time (2 hr) and 0.10% initiator). For SPA, better hysteresis was achieved at lower SPA concentrations.

TABLE 1

| Ex # | Reactive Anionic Monomer (0.045 mol) | Rxn Temp. (° C.) | Time (hr) | % CAN | Adv. CA (°) | Rec. CA (°) | Hysteresis (°) |
|---|---|---|---|---|---|---|---|
| Nelfilcon lenses | | | | | | | |
| CE1 | ex packing | — | — | — | 44 | 15 | 29 |
| CE2 | Saline washed* | | | | 66 | 34 | 32 |
| 1 | SPA | 40 | 1 | 0.05 | 46 | 44 | 2 |
| 2 | | | 1 | 0.10 | 52 | 45 | 7 |
| 3 | | | 2 | 0.05 | 41 | 37 | 4 |
| 4 | | | 2 | 0.10 | 40 | 38 | 2 |
| 5 | SPA/TRIS | 40 | 1 | 0.05 | 65 | 33 | 32 |
| 6 | NaAMPS | 40 | 1 | 0.05 | 44 | 37 | 7 |
| 7 | | | 1 | 0.10 | 52 | 33 | 19 |
| 8 | NaAMPS/TRIS | 40 | 1 | 0.05 | 49 | 26 | 23 |
| 9 | TRIS | 40 | 1 | 0.05 | 40 | 38 | 2 |
| 10 | NaAMPS/SPA | 40 | 1 | 0.05 | 43 | 39 | 4 |
| Lenefilcon lenses | | | | | | | |
| CE3 | — | — | — | — | 54 | 35 | 19 |
| 11 | SPA | 40 | 1 | 0.05 | 46 | 40 | 6 |
| 12 | | | 1 | 0.10 | 57 | 36 | 21 |
| 13 | | | 2 | 0.05 | 46 | 35 | 11 |
| 14 | | | 2 | 0.10 | 58 | 38 | 20 |
| 15 | SPA/TRIS | 40 | 1 | 0.05 | 68 | 34 | 34 |
| 16 | NaAMPS | 40 | 1 | 0.05 | 53 | 21 | 32 |
| 17 | | | 1 | 0.10 | 50 | 40 | 10 |
| 18 | | 50 | 2 | 0.10 | 18 | 13 | 5 |
| 19 | | 60 | 2 | 0.10 | 42 | 36 | 6 |
| 20 | NaAMPS/TRIS | 40 | 1 | 0.05 | 82 | 21 | 61 |
| 21 | TRIS | 40 | 1 | 0.05 | 62 | 36 | 36 |
| Polymacon lenses | | | | | | | |
| CE4 | — | — | — | — | 107 | 41 | 66 |
| 22 | SPA | 40 | 1 | 0.05 | 86 | 41 | 45 |
| 23 | NaAMPS | 40 | 1 | 0.05 | 102 | 40 | 62 |

The lenses from Examples 1, 2, 6, 7, 12, 16, 17, 22 and 23 were tested for the presence of sulfur as an indication of physical proof of grafting.

For each of the grafted lenses, sulfur was detected in the lenses of Examples 1, 2, 6, 7, 12, 16 and 17. Sulfur was not detected on the lens of Examples 22 and 23 (SeeQuence/SPA), which may have been a peculiarity of the sample or a sign of irregular grafting. On the majority of the spectra, cerium (the initiator) was also noticeable. Sulfur was not present on any of the non-grafted control lenses.

It is believed that the chemical nature of the (polyvinyl alcohol-based) nelfilcon lens, which has a higher number of surface hydroxyl groups, provides more reactive sites for the grafting polymerization, which accounts at least in part for the significantly improved hysteresis displayed in Examples Examples 24-27 and Comparative Examples 5-7

Ungrafted nelfilcon lenses from Comparative Example 2 and lenses of Examples 3, 6 and 10 were placed into a 5 cm×5 cm glass cell and taken through identical humidity cycles, using an automated dynamic vapour sorption analyser (DVS). A schematic of this system is shown in FIG. 1. At the heart of the DVS system was an ultra-sensitive microbalance, 1, (Micrbalance Cahn D-200) capable of measuring changes in sample mass to less than 1 part in 10 million. The microbalance was housed in a precisely controlled constant temperature incubator, 2, which ensured very high baseline stability as well as accurate control of the relative humidity. Dry gas flow was controlled via mass flow controller 3 and saturated vapour gas flows were controlled using mass flow controller 5, and vapour humidifier, 5. Humidity and temperature probes, 6, were situated just below the sample and reference holders, 7 and 8, respectively, to give independent verification of system performance. The DVS was fully automated under control from a dedicated microcomputer, not shown.

The conditions in the chamber were controlled as follows, temperature was maintained at 25° C. and humidity was controlled in a cycle of 40 minutes at 98% relative humidity, followed by 2 minutes at 40% relative humidity for 100 minutes.

Figure 2:
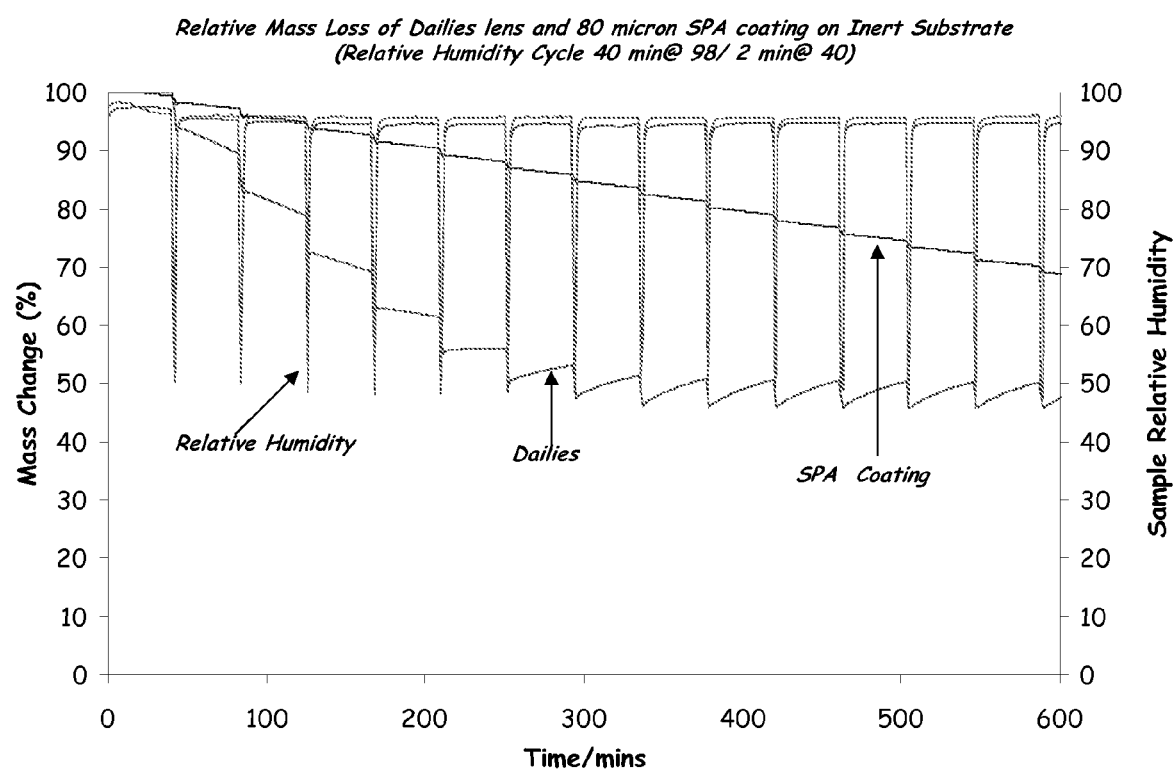
FIG. 2 is a graph of the relative mass loss of control lenses and lenses of the present invention as a function of time.

After the full humidity cycle, the glass cells containing the lenses were removed from the DVS cabinet and placed on the stage of an image-capture sessile drop contact angle apparatus (Digidrop Contact Angle Meter, GBX Scientific Instruments, Romans, France) located next to the DVS cabinet and the change in contact angle was monitored. The results are shown in FIG. 2. As shown in FIG. 2, the unmodified lenses showed a marked and progressive fall in contact angle as the surface rehydrated whereas the grafted lenses of the present invention retained a higher degree of hydration showed a much lower initial contact angle and little further change.

FIG. 2 shows that the lenses coated with ionic SPA and AMPS monomers showed a greater affinity for water than do the untreated hydrogels. The grafted layer did not prevent dehydration of the lens, but it appears, maintained a higher degree of hydration and rehydrated preferentially.

Comparative Examples 8-11

Figure 3:
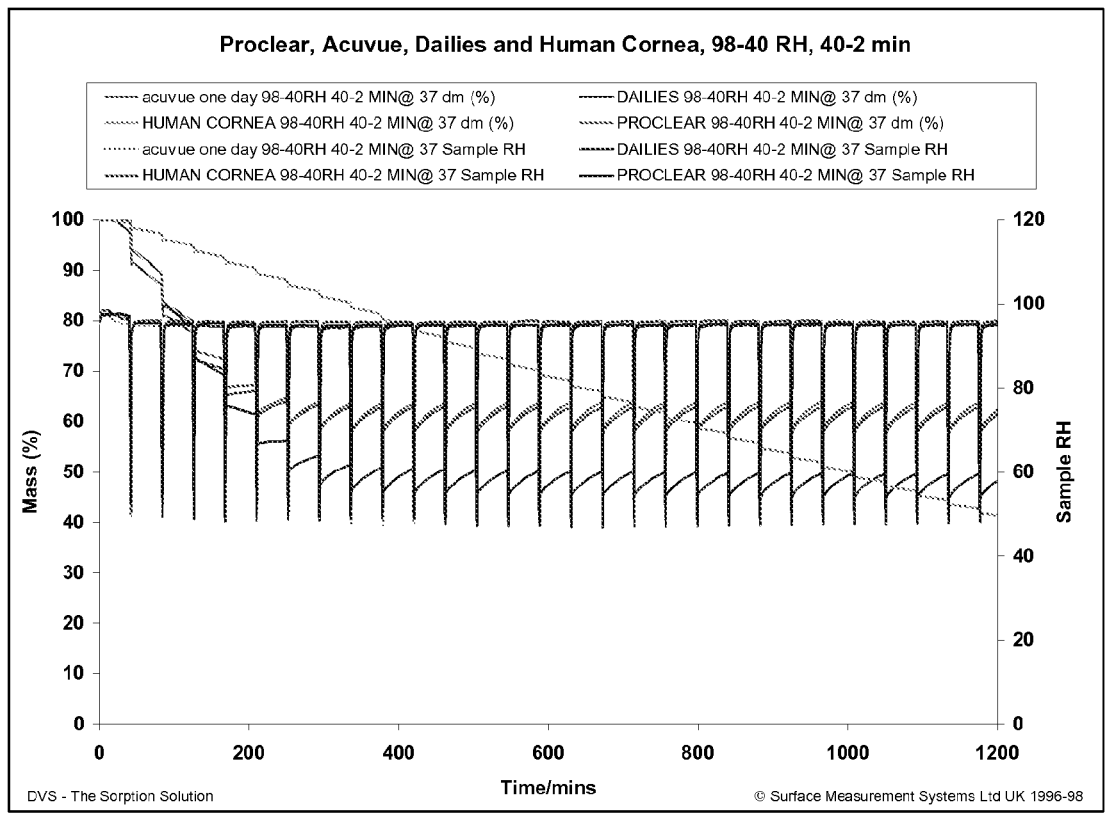
FIG. 3 is a graph of the relative mass loss of three commercially available lenses and a sample of healthy human cornea as a function of time.

The dehydration/rehydration dynamics of commercially available untreated lenses (ACUVUE ONE DAY® brand contact lenses (commercially available from Vistakon), DAILIES® brand contact lenses (commercially available from CibaVision) and BIOCOMPATIBLE PROCLEAR® brand contact lenses), and human cornea were measured using the automated dynamic vapour sorption analyser (DVS) described in Examples 24-27, above. For each lens measured, the lens was placed in the sample holder, excess moisture was removed, and the relative mass loss of sample was measured at regular intervals throughout the humidity cycle. FIG. 3 shows the results from the analysis of three commercially available lenses. A sample of healthy human cornea was tested using the same procedure.

Examples 28-29

Etafilcon lenses (ACUVUE brand contact lenses, commercially available from Vistakon) were removed from their packaging and rinsed with distilled deionized water to remove saline. A coating solution was made having the components in the amounts shown in Table 2, below.

TABLE 2

| Component | Ex 28 | Ex 29 |
|---|---|---|
| Water (HPLC grade) | 100 g | 100 g |
| SPA | 10.44 gm | 0 |
| NaAMPS | 0 | 7.90 g |
| PEG-acrylate | 0 | 1.50 g |
| CAN | 0.15 | 0.15 |
| Kpersulfate | 0.5 | 0 |
| MbA | 0.13 | 0.13 |

The monomer(s) (anionic monomer and comonomer if used) were dissolved in 50 gm of water, and nitrogen was bubbled through the solution for 10 minutes. The CAN, potassium persulfate and MbA were dissolved in the other 50 gm of water. The lenses to be coated were immersed in the CAN solution, and the monomer solution was added to the CAN solution to form the coating solution. Nitrogen was bubbled through the coating solution. The mixture was kept at 50° C., and a constant stream of nitrogen was bubbled through the coating solution. After 4 hours the lenses were removed from the coating solution and then washed with distilled water for 20 minutes with gentle stirring. The wash solution was replaced with fresh distilled water and the wash step was repeated. The coated lenses were placed in small vials containing saline solution (pH 7.4), sealed and sterilized at about 120° C. for about 20 minutes.

The hysteresis for the coated and uncoated lenses were measured. The hysteresis for the SPA coated lenses was 3, compared to the hysteresis of 26 for the uncoated etafilcon lenses.

Examples 30-31

The lenses made in Examples 28-29 above were clinically evaluated against untreated ACUVUE® ONE DAY brand contact lenses (etafilcon A). The clinical evaluation was a single masked (patient), randomized, study with twenty patients completing the study.

The enrolled patients met the following criteria: aged 18 years or great, habitual daily soft contact lens wearers, with a best visual acuity of at least 6/9, symptomatic score>0.19 on CLDEQ (Nichols et al., 2002) and willing to adhere to the instructions set in the clinical protocol. The subjects were non-astigmatic (<1 DC) and free of ocular allergies, disease, active ocular infection, significant (Efron grade 3 or greater) ocular tissue anomaly and not currently using any ocular medication or systemic medication with ocular implications.

The patients wore the three lens types in a random order for 3 days, with assessment made on the afternoon of the third day. A minimum two day period was allowed before the next lens type was evaluated.

Bulbar hyperaemia, palpebral roughness and corneal staining were graded using the CCLRU grading scale to 0.1 scale unit resolution. No microcysts, straie, folds or infiltrates were observed during the trial.

The patients rated the lenses on a continuous visual analogue scale for the following parameters: comfort, dryness, burning/stinging, visual clarity and photophobia. The ratings were made upon insertion (first 30 minutes of wear), daytime (rest of the day up to 6 pm) and evening (from 6 pm to contact lens removal) in a log book. Tables 3-5 shows the study results. Patients also recorded the number of hours the lenses were worn. The average reported wear time for the lenses was as follows: Example 30 (SPA-coated lenses of Example 28) 11.05±2.81 hours, Example 31 (AMPS-coated lenses of Example 29) for 12.01±2.45 hours and control lenses of Comparative Example 12 (uncoated etafilcon lenses) for 10.90±2.79 hours per day.

TABLE 3

Subjective Ratings upon insertion

| | Comfort | | Dryness | | Vision | |
|---|---|---|---|---|---|---|
| Ex. # | M | SD | M | SD | M | SD |
| 30 | 78 | 22 | 83 | 17 | 77 | 26 |
| 31 | 88 | 15 | 86 | 14 | 88 | 16 |
| Uncoated | 75 | 23 | 78 | 19 | 81 | 21 |

TABLE 4

| | Daytime subjective ratings | | | | | |
| --- | --- | --- | --- | --- | --- | --- |
| | Comfort | | Dryness | | Vision | |
| Ex. # | M | SD | M | SD | M | SD |
| 30 | 71 | 27 | 73 | 25 | 70 | 31 |
| 31 | 80 | 20 | 74 | 27 | 94 | 98 |
| Uncoated | 66 | 29 | 64 | 29 | 69 | 31 |

TABLE 5

| | Evening subjective ratings | | | | | |
| --- | --- | --- | --- | --- | --- | --- |
| | Comfort | | Dryness | | Vision | |
| Ex # | M | SD | M | SD | M | SD |
| 30 | 59 | 30 | 58 | 31 | 65 | 33 |
| 31 | 76 | 27 | 72 | 29 | 80 | 21 |
| Uncoated | 58 | 32 | 54 | 32 | 67 | 31 |

The lenses of the present invention displayed comfort, dryness and vision which were at least as good, and in the case of Example 31, better than the uncoated control. All lenses displayed acceptable movement and low staining.

Example 32

8 g (5.38% wt) of 2-hydroxyethyl acrylamide (in the form of a 45% solution in water), 40.0 g (49.80% wt) of sodium 2-acrylamido 2,2 methylpropane sulphonate, (in the form of a 50% solution in water) and 16.01 g (44.82% wt) of N-vinyl pyrrolidone together with 0.8 g (2% wt) of potassium persulphate ($K_2S_2O_8$) initiator were dissolved in a mixture of 80 mls of acetonitrile and 120 mls of water. The mixture was introduced into a three-necked reaction flask equipped with stirrer, water condenser and nitrogen sparge and heated by an electric isomantle. The reaction mixture was heated to a temperature of 70° C. for a period of 60 minutes. The reaction mixture was precipitated into an excess volume of acetone, filtered and dried in a vacuum oven at 60° C. giving a 67% yield (26.5 g).

Recovered polymer was dissolved in PBS to form a 0.01 wt % solution of polymer. The polymer dissolved readily with gentle agitation on an orbital shaker. 100 ml of the 0.1% polymer solution was added to a 200 ml autoclavable polypropylene plastic screwtop container. 1DAY ACUVUE brand contact lenses, commercially available from Johnson & Johnson Vision Care, Inc. were placed into Histosette biopsy cassettes. Three Hisosette cassesttes were placed into a 200 ml plastic screwtop container, and the container top was screwed on. The container was placed into an autoclave. The container and lenses were autoclaved in the 0.1% polymer solution for 30 minutes at 120° C. The containers were removed from the autoclave and the polymer solution replaced by PBS. The lenses in the Histocassetes were washed/stored in PBS for at least two days before performing the COF analysis, with at least two changes of PBS. Tweezers were used to handle and transfer the lenses. Lenses were found to have maintained their original dimensions following this process.

The coefficient of friction of the lenses was measured as follows. A high sensitivity tribometer (CSM Nano Scratch Tester, CSM Instruments, Peseux, Switzerland) mounted on an air table was used for the measurement of coefficient of friction. The test lens was placed on a convex support and the coefficient of friction measured as the lens slides at a sliding speed of 5 mm/minute under a load of 3 mN/m a chosen substrate (Melinex® (polyethylene terephthalate) film (DuPont) in the presence of a lubricating solution (Hypotears® artificial tear solution (Novartis Ophthalmics).

For each sample ten repeat runs of 20 mm distance was measured. At least two lenses were run under these conditions and the data from the lenses were averaged. The COF for the lenses of this Example 32 were 0.161±0.013.

Comparative Example 8

Example 32 was repeated, except that PBS without any polymer was used as the sterilization solution. The COF of the untreated lenses was measured to be 0.47.

Examples 33-42

Example 32 was repeated using the components and conditions listed in Table 6-8 below. COF was measured for Examples 36, 37, 39, 40, 42, 44, 45, 47, 49, 50 and 52, and is shown in Table 9, below.

TABLE 9

| Ex # | COF |
| --- | --- |
| 36 | 0.224 |
| 37 | 0.204 |
| 39 | 0.224 |
| 40 | 0.175 |
| 42 | 0.295 |
| 44 | 0.262 |
| 45 | 0.229 |
| 47 | 0.143 |
| 49 | 0.291 |
| 50 | 0.162 |
| 52 | 0.200 |

Thus, compared to the control which had a COF of 0.47, the lenses of the present invention displayed significant improved COF.

TABLE 6

| Ex# | HEA | NaAMPS | NVMA | ACMO | NVP | DMA | HEAc | $K_2S_2O_8$ | Vol (ml) | Rxn time (min) | Evd. polym | PPT | PPT prod (g) | % conv |
| --- | --- | --- | --- | --- | --- | --- | --- | --- | --- | --- | --- | --- | --- | --- |
| 33 | 9.06 | 40.08 | 8 | 8.02 | 0 | 0 | 0 | 0.4 | 200 | 150 | PA | yes | 17.35 | 43.2 |
| 34 | 0 | 40.03 | 8.03 | 8.07 | 0 | 0 | 4.11 | 0.4 | 200 | 150 | PA | Yes | NM | NM |
| 35 | 0 | 40.6 | 8.09 | 8.08 | 0 | 0 | 4.0 | 0.4 | 200 | 120 | PA | Yes | NM | NM |
| 36 | 0 | 39.98 | 8.01 | 8.01 | 0 | 0 | 4.12 | 0.4 | 200 | 90 | VR* | Yes | 10.38 | 54[1] |
| 37 | 9.53 | 40.01 | 8.03 | 8.03 | 0 | 0 | 0 | 0.4 | 200 | 150 | VR | yes | 14.02 | 34.8 |
| 38 | 2 | 10 | 2 | 0 | 2 | 0 | 0 | 0.2 | 100 | | | NT | NM | NM |
| 39 | 4.5 | 20 | 12 | 12 | 0 | 0 | 0 | 0.8 | 200 | 60 | VR*, PA | Yes | 20.07 | 55.4 |
| 40 | 4.5 | 60 | 4 | 4 | 0 | 0 | 0 | 0.8 | 200 | 25 | VR, | Yes | 13.36 | 66.8[1] |

TABLE 6-continued

| Ex# | HEA | NaAMPS | NVMA | ACMO | NVP | DMA | HEAc | K₂S₂O₈ | Vol (ml) | Rxn time (min) | Evd. polym | PPT | PPT prod (g) | % conv |
|---|---|---|---|---|---|---|---|---|---|---|---|---|---|---|
| 41 | 2.4 | 20 | 0 | 0 | 0 | 9 | 0 | 0.4 | 200 | 90 | PA VR, PA | yes | 14.82 | 73.8 |
| 42 | 0.5 | 10 | 2.25 | 0 | 0 | 2.25 | 0 | 0.2 | 100 | 10 | PA | yes | 3.07 | 31.6 |

PA = precipitate in acetone
VS = viscosity rise
*greasy lines observed
¹only half of solution precipitated
NM = not measured
NT = not tried

TABLE 7

| Ex# | HEA | NaAMPS | NVMA | Am | NIPAm | THFA | DMA EMA | NVA | K₂S₂O₈ | Vol (ml) | Rxn time (min) | Evd. polym | PPT | PPT prod (g) | % conv |
|---|---|---|---|---|---|---|---|---|---|---|---|---|---|---|---|
| 43 | 2 | 10 | 2 | 2 | 0 | 0 | 0 | 0 | 0.2 | 100 | 90 | PA | yes | NM | NM |
| 44 | 8 | 40 | 8 | 0 | 4 | 0 | 0 | 0 | 0.8 | 200 | 90 | Pink*, PA | Yes | yes | 10.43 |
| 45 | 6.12 | 41.19 | 8.01 | 0 | 0 | 10.18 | 0 | 0 | 0.2 | 200 |  | Color, PA | Yes | 10.35 | 49.81¹ |
| 46 | 1.59 | 10.52 | 2.15 | 0 | 0 | 0 | 2.91 | 0 | 0.2 | 100 | 90 | PA | Yes | NM | NM |
| 47 | 8 | 40 | 8 | 0 | 0 | 0 | 0 | 8 | 0.8 | 200 | 90 | PA | yes | NM | NM |
| 48 | 8 | 15 | 15.5 | 0 | 0 | 0 | 0 | 15.5 | 0.8 | 200 | 90 | PA | Yes | NM | NM |

PA = precipitate in acetone
VS = viscosity rise
*greasy lines observed
¹only half of solution precipitated
NM = not measured

TABLE 8

| Ex# | HEA | SPA | NVMA | ACMO | NaVS | K₂S₂O₈ | Vol (ml) | Rxn time (min) | Evd. polym | PPT | PPT prod (g) | % conv |
|---|---|---|---|---|---|---|---|---|---|---|---|---|
| 49 | 10.07 | 20.58 | 8.55 | 8.37 | 0 | 0.8 | 200 | 90 | *PA | yes | 10.17 | 48.38¹ |
| 50 | 9.68 | 0 | 8.05 | 8.08 | 66.86 | 0.8 | 200 | 90 | Color, PA | Yes | NM | NM |
| 51 | 8 | 20 | 8 | 0 | 0 | 0.8 | 100 | 90 | PA | Yes | NM | 39.6 |
| 52 | 8 | 0 | 8 | 0 | 67 | 0.8 | 100 | 90 | PA | Yes | NM | 39.7 |

PA = precipitate in acetone
*greasy lines observed
¹only half of solution precipitated
NM = not measured

We claim:

1. A composition comprising a polymer comprising at least one volume excluding polymer formed from a reaction mixture comprising from about 30 to about 60 weight % at least one reactive anionic monomer comprising at least one hydratable polyanion group; about 15 to about 45 wt % at least one amide containing comonomer, about 10 to about 30 wt % at least one carboxylic acid containing comonomer and about 10 to about 30 wt % at least one hydroxyl containing comonomer.

2. The composition of claim 1 wherein said hydratable polyanion group is distributed substantially uniformly throughout said volume excluding polymer.

3. The composition of claim 2 wherein said reactive anionic monomers are of the formula:

R-L-A wherein R is a reactive group, L is a linking group and A is a hydratable polyanion group.

4. The composition of claim 3 wherein R is a free radical reactive group selected from the group consisting of (meth)acrylates, styryls, vinyls, vinyl ethers, $C_{1-6}$alkyl(meth)acrylates, (meth)acrylamides, $C_{1-6}$alkyl(meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates.

5. The composition of claim 3 wherein R is a free radical reactive group selected from the group consisting of (meth)acrylate, acryloxy, (meth)acrylamide, and mixtures thereof.

6. The composition of claim 3 wherein R is selected from the group consisting of vinyl ethers or epoxide groups, alcohols, esters, carboxylic acids, isocyanates, anhydrides, groups capable of halide displacement, cyclic derivatives of hydroxyl and amino carboxycylic acids, cyclic ethers, cyclic esters, cyclic amides and combinations thereof.

7. The composition of claim 3 wherein L is selected from the group consisting of substituted and unsubstituted alkylene having 1-12 carbon atoms, which may be straight or branched, polyethers, oxazolines, substituted and unsubstituted heterocyclic groups and combinations thereof.

8. The composition of claim 3 wherein A is selected from the group consisting of phosphates, phosphonates, borates, sulfates, sulfonates and combinations thereof.

9. The composition of claim 3 wherein A comprises at least one sulfonate group.

10. The composition of claim 1 wherein said reactive anionic monomers have the formula

$H_2C=C(R_2)-CO_2-(CH_2)_n-A$ wherein $R_2$ is selected from —H, —$CH_3$, —$CH_2CO_2$—$(CH_2)_n$-A, where n is an integer between 2 and 8 and A is a hydratable polyanion group.

11. The composition of claim 10 wherein A is selected from the group consisting of phosphates, phosphonates, borates, sulfates, sulfonates and combinations thereof.

12. The composition of claim 10 wherein A comprises at least one sulfonate group.

13. The composition of claim 1 wherein said volume excluding polymer is an oligomer having a molecular weight of at least about 500.

14. The composition of claim 1 comprising at least two volume excluding polymers, a first volume excluding polymer having a molecular weight of less than about 10,000 and a second volume excluding polymer having molecular weight of greater than about 100,000.

15. The composition of claim 2 further comprising at least one physiologically compatible cation anionically bound to said polyanion groups.

16. The composition of claim 15 wherein said cation is selected from the group consisting of Li+, Na$^+$, K$^+$, NH$_4^+$, Mg$^+$, Zn$^+$, Ag+, and combinations thereof.

17. The composition of claim 15 wherein said cation is selected from the group consisting of Na$^+$, K$^+$ and mixtures thereof.

18. The composition of claim 1 wherein said reactive anionic monomers is selected from the group consisting of sodium-2-(acrylamido)-2-methylpropane sulphonate, 3-sulphopropyl (meth)acrylate potassium salt, 3-sulphopropyl (meth)acrylate sodium salt, 3-sulphopropyl (meth)acrylate calcium salt, di-potassium salt of bis-3-sulfopropylester (meth)acrylate, di-calcium salt of bis-3-sulfopropylester (meth)acrylate, di-sodium salt of bis-3-sulfopropylester (meth)acrylate, styrene sulfonate and mixtures thereof.

19. The composition of claim 1 wherein said at least one-amide-containing comonomer has the structure

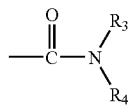

where $R_3$ and $R_4$ are independently selected from H, straight or branched $C_{1-12}$ alkyls which may be ether substituted.

20. The composition of claim 1 wherein said comonomers comprises hydrophilic monomers selected from the group consisting of N,N-dimethylacrylamide, 2-hydroxyethyl methacrylate, glycerol methacrylate, 2-hydroxyethyl methacrylamide, N-vinyl pyrrolidone, N-vinyl-N-methyl acrylamide, N-methyl-N-vinylacetamide, polyethyleneglycol monomethacrylate, methacrylic acid, acrylic acid, N-(tris(hydroxymethyl)methyl)acrylamide, itaconic acid and combinations thereof.

21. The composition of claim 1 wherein said volume excluding polymer has a structure selected from the group consisting of brush structure, branched structure, looped structure, or a combination thereof.

22. The composition of claim 1 wherein said volume excluding polymer forms an interpenetrating network with at least a portion of said polymer.

* * * * *